(12) United States Patent
Lukas et al.

(10) Patent No.: US 9,101,762 B2
(45) Date of Patent: Aug. 11, 2015

(54) PATIENT IRRADIATION APPARATUS HAVING SIMPLIFIED PATIENT ACCESS

(75) Inventors: Jörg Lukas, Dresden (DE); Dieter Wöhrl, Kastl (DE)

(73) Assignee: Siemens Aktiengesellschaft, München (DE)

(*) Notice: Subject to any disclaimer, the term of this patent is extended or adjusted under 35 U.S.C. 154(b) by 654 days.

(21) Appl. No.: 13/485,882

(22) Filed: May 31, 2012

(65) Prior Publication Data
US 2012/0307979 A1 Dec. 6, 2012

(30) Foreign Application Priority Data

Jun. 1, 2011 (DE) .......................... 10 2011 076 876

(51) Int. Cl.
*A61B 6/04* (2006.01)
*A61N 5/10* (2006.01)
*G21K 1/02* (2006.01)
*G21K 1/04* (2006.01)

(52) U.S. Cl.
CPC ................. *A61N 5/1049* (2013.01); *G21K 1/02* (2013.01); *G21K 1/04* (2013.01); *A61B 6/0407* (2013.01)

(58) Field of Classification Search
CPC ...... A61B 6/0407; A61B 6/04; A61B 6/0457; A61B 6/4476; A61N 2005/1061
USPC ............... 378/177, 195, 196, 208, 189; 5/601
See application file for complete search history.

(56) References Cited

U.S. PATENT DOCUMENTS

| | | | | |
|---|---|---|---|---|
| 4,024,403 | A * | 5/1977 | Bernstein et al. | 378/177 |
| 4,293,770 | A * | 10/1981 | Vavrek | 378/196 |
| 5,416,824 | A * | 5/1995 | Goldhorn et al. | 378/189 |
| 5,515,415 | A | 5/1996 | Herrmann et al. | |
| 5,953,776 | A | 9/1999 | Sanders et al. | |
| 7,428,295 | B2 * | 9/2008 | Fehre et al. | 378/108 |
| 7,938,578 | B2 | 5/2011 | Beimler et al. | |
| 2006/0269044 | A1 | 11/2006 | Fehre et al. | |
| 2009/0296891 | A1 * | 12/2009 | Beimler et al. | 378/167 |
| 2011/0067179 | A1 | 3/2011 | Klemm et al. | |

FOREIGN PATENT DOCUMENTS

| | | |
|---|---|---|
| CN | 2342773 Y | 10/1999 |
| CN | 1915172 A | 2/2007 |

(Continued)

OTHER PUBLICATIONS

German Office Action dated Jan. 26, 2012 for corresponding German Patent Application No. DE 10 2011 076 876.9 with English translation.

(Continued)

*Primary Examiner* — David J Makiya
*Assistant Examiner* — John Corbett
(74) *Attorney, Agent, or Firm* — Lempia Summerfield Katz LLC

(57) ABSTRACT

An apparatus for irradiating patients with x-ray radiation is provided. The apparatus includes a lowerable patient support and an x-ray apparatus that may be positioned below the lowerable patient support. The apparatus is configured such that part of the x-ray apparatus is moved into the lowerable patient support when the patient support is lowered. The lowerable patient support may be lowered further, thereby facilitating access for the patient.

20 Claims, 11 Drawing Sheets

(56) References Cited

FOREIGN PATENT DOCUMENTS

| DE | 10 2005 020 898 A1 | 11/2006 |
| DE | 10 2008 025 242 A1 | 12/2009 |
| WO | WO 98/27866 | 7/1998 |

OTHER PUBLICATIONS

Not in English—Only search report on p. 5 of 6 of Chinese action considered. Chinese Office Action for Chinese Application No. 201210176571.1, mailed Mar. 31, 2015, with German Translation.

* cited by examiner

US 9,101,762 B2

PATIENT IRRADIATION APPARATUS HAVING SIMPLIFIED PATIENT ACCESS

This application claims the benefit of DE 10 2011 076 876.9, filed on Jun. 1, 2011.

BACKGROUND

The present embodiments relate to an apparatus for irradiating patients with x-ray radiation.

In medical technology, x-rays may be used for diagnosis and therapy. The design and mechanics of x-ray devices may be adjusted for the desired functions. Functions of this type are, for example, the conventional x-ray diagnostics with the recording of individual x-ray images, fluoroscopy, mammography and computed tomography. With fluoroscopy, contrary to conventional x-ray diagnostics, no static individual image is produced. Instead, dynamic processes in the body are made visible by brief snapshots or whole series of individual images such as, for example, swallowing or the movement of the esophagus. In fluoroscopic systems, a distinction may be made between under-couch devices and/or under-couch systems that position the x-ray tube below the patient couch, and over-couch systems, in which the x-ray tube is attached above the couch.

SUMMARY AND DESCRIPTION

The present embodiments may obviate one or more of the drawbacks or limitations in the related art. For example, patient access to x-ray apparatuses may be facilitated.

With under-couch devices having x-ray emitters fixedly mounted below the patient support, the latitude available for lowering the patient support is limited. In order to achieve optimal illumination and separation from the image receiver, the x-ray emitter requires a specific distance. A floor-to-patient support distance that may not be downwardly changed may result therefrom. It may not be comfortable for the patient to climb onto the couch when the minimal couch height of approximately 80 to 90 cm is restricted by the fixed x-ray emitters. This applies to patients who are not in a good state of health. In accordance with the present embodiments, an apparatus that includes a lowerable patient support and an x-ray apparatus that may be positioned below the patient support is provided in order to irradiate patients with x-rays. Provision is made for the accommodation and/or lowering of at least one part of the x-ray apparatus in the patient support for the purpose of further lowering the patient support. This apparatus is an under-couch device, for example.

The ability to lower part of the x-ray apparatus in the patient support may reduce the minimal patient support height. The patient is thus helped with climbing onto the patient support, so that less assistance has to be provided by hospital personnel. Any climbing aids provided in conventional devices may be dispensed with.

The x-ray apparatus is an apparatus for generating x-rays. The x-ray apparatus may be formed with an x-ray emitter and an aperture housing. According to one embodiment, part of the aperture housing is accommodated in the patient support when the patient support is being lowered.

In one embodiment, a mechanism that establishes a releasable contact between the patient support and the x-ray apparatus such that the x-ray apparatus is also subject to a vertical change in position of the patient support is provided. The releasable contact is disengaged for the lowering of the at least one part of the patient apparatus in the patient support such that the patient support and the x-ray apparatus may be displaced relative to one another. Contact may be established in a first phase of the lowering, and the patient support may be lowered together with the x-ray apparatus. A maximum value of the possible shared mutual lowering is achieved during the first phase, whereupon the contact is released, and a further lowering of the patient support is connected with a lowering and/or displacement of part of the x-ray apparatus in the patient support. The release of the contact between the patient support and the x-ray apparatus may be triggered by a force counteracting the lowering. This force is conveyed, for example, by the x-ray emitter landing on the floor. A sensor system may be provided, for example, connecting a light barrier that detects a threshold value for the height of the patient support and triggers a release of the contact. The lowering with existing contacts may be braked in a final phase. Both the release of contact triggered by a sensor and also the braking may be used to reduce any force effects (e.g., by the floor) when reaching the final position of a first phase of the lowering process in order to prevent damage to the x-ray apparatuses. The second phase of lowering includes displacing part of the x-ray apparatus in the patient support.

In one embodiment, the mechanism may be configured to manufacture the contact in a defined relative position of the patient support and the x-ray apparatus. This is realized, for example, by a mechanism that includes a detent and a detent lever. In this embodiment, the detent lever is pressed out of the detent during the course of the release of the contact, and the contact is established by a renewed engagement. The function of reestablishing the contact is meaningful with respect to raising the patient support in order to achieve a recording position for the x-ray recording.

In one embodiment, a safety system may be provided. The safety system detects whether the contact is established. The x-ray direction is blocked for x-ray recordings by the safety system, provided there is no contact. With a released contact and/or partially inserted x-ray apparatus, the optimal distances between the x-ray emitter and the patient for an x-ray recording are not present. An intentional triggering of an x-ray recording may be explicitly prevented.

The raising or lowering of the x-ray emitter may be realized by a motor that is arranged laterally to the aperture housing, for example. "Laterally" may be an area of the entire plane at right angles to the beam direction (e.g., an arrangement behind the aperture housing).

DETAILED DESCRIPTION OF THE DRAWINGS

Figure 1:
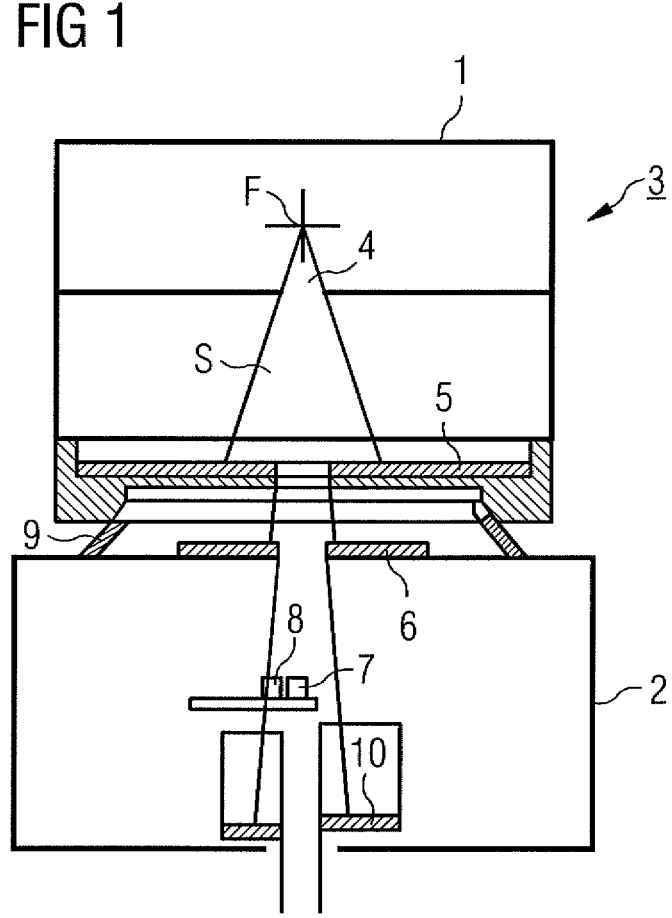
FIG. 1 shows a conventional x-ray apparatus.

FIG. 1 shows an apparatus 3 for generating x-rays. The apparatus 3 includes an x-ray emitter 1 and an aperture housing 2. The x-ray emitter 1, from which focus F x-rays emanate, includes a rough pre-aperture 5 and a beam window 4. A pre-aperture 6 provided with the slots and elements 7 and 8 for determining a position of the focus F and an actual main aperture 10 for forming a useful x-ray beam bundle are integrated into the aperture housing 2. In order to protect against radiation, a scattered radiation seal 9 also exists between the x-ray emitter 1 and the aperture housing 2. With an under-couch device, the x-ray apparatus 3 radiates upwards (e.g., a position is rotated by 180 degrees with respect to FIG. 1).

The x-ray apparatus 3 exhibits an expansion in the beam direction. The aperture structure is responsible for a minimum distance of the focus F from a patient being provided during operation. In conventional under-couch devices, this distance limits the possible lowering depth of the patient support and/or patient couch. As a result, access for the patient is made more difficult. The patient may climb onto a couch with a couch height of approximately 80 to 90 cm. This is difficult for many patients with respect to the size and/or state of health of the patient. To remedy this difficulty, present embodiments are explained in more detail below with the aid of FIG. 2.

Figure 2:
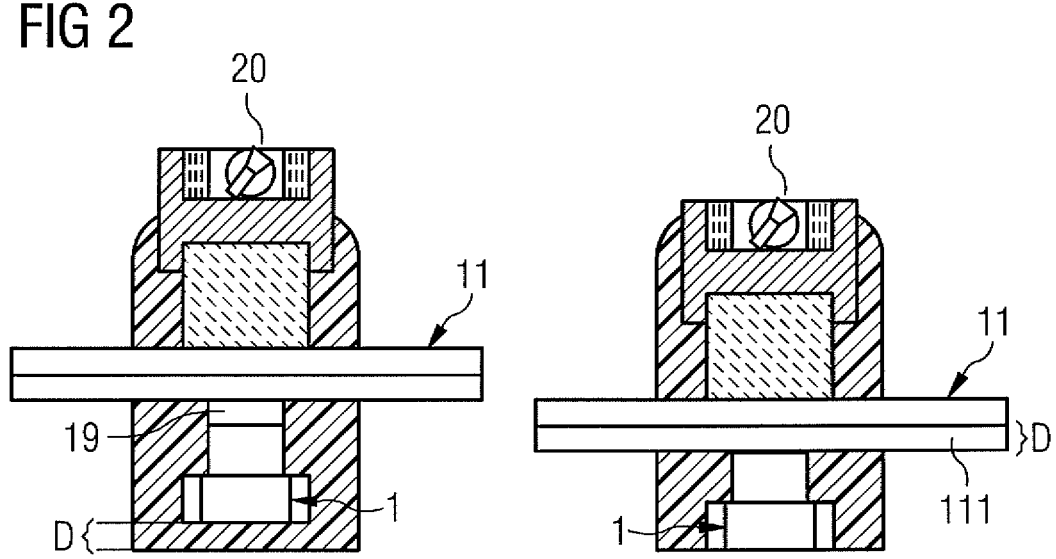
FIG. 2 shows one embodiment of an under-couch device in two different positions.

FIG. 2 shows one embodiment of an under-couch device 20 in two different positions. A position, in which recordings take place, is shown on the left side. The x-ray emitter 1 is a certain distance from the floor and is arranged for fluoroscopy with respect to the patient support 11. In order to enable the patient to climb onto the patient support 11, the patient support 11 is lowered as shown in the image to the right. The x-ray emitter 2 is lowered to the floor. The x-ray apparatus includes an area 19 that is accommodated when lowering the patient support 11 in a lower region 111 of the patient support 11. The patient support 11 may therefore be lowered further than with conventional systems by about the thickness D of the lower area 111. The patient support 11 is thus more easily accessible.

Figure 3:
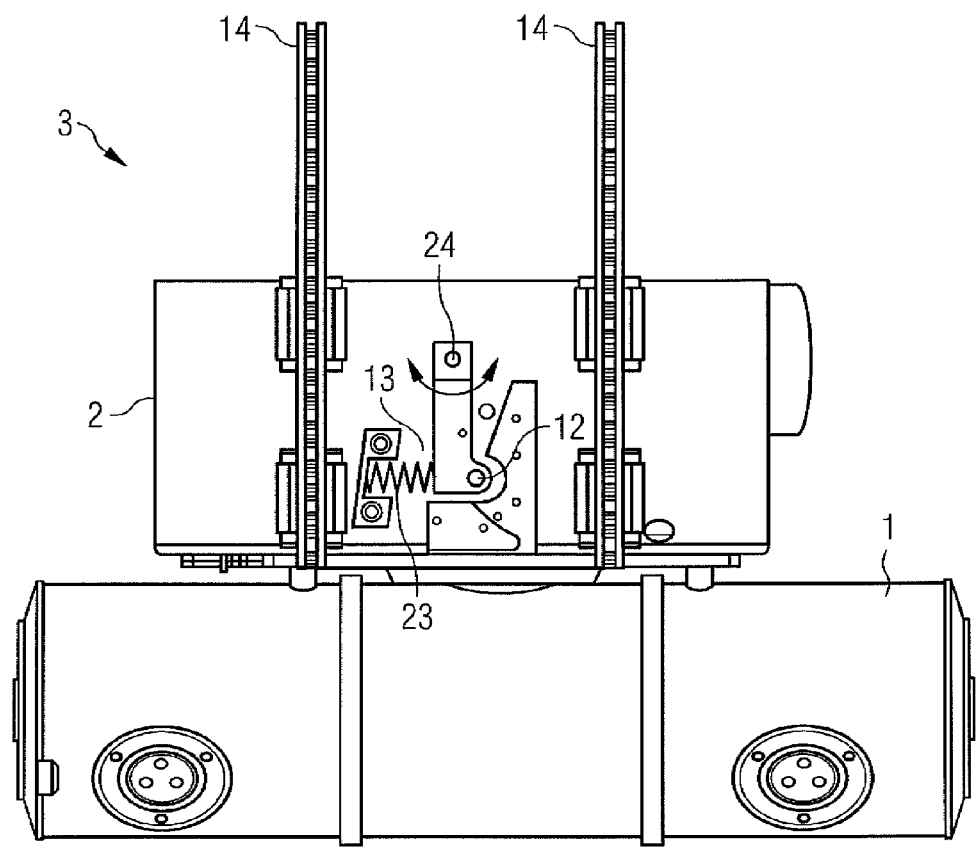
FIG. 3 shows one embodiment of an x-ray apparatus having an engaging mechanism.
Figure 4:
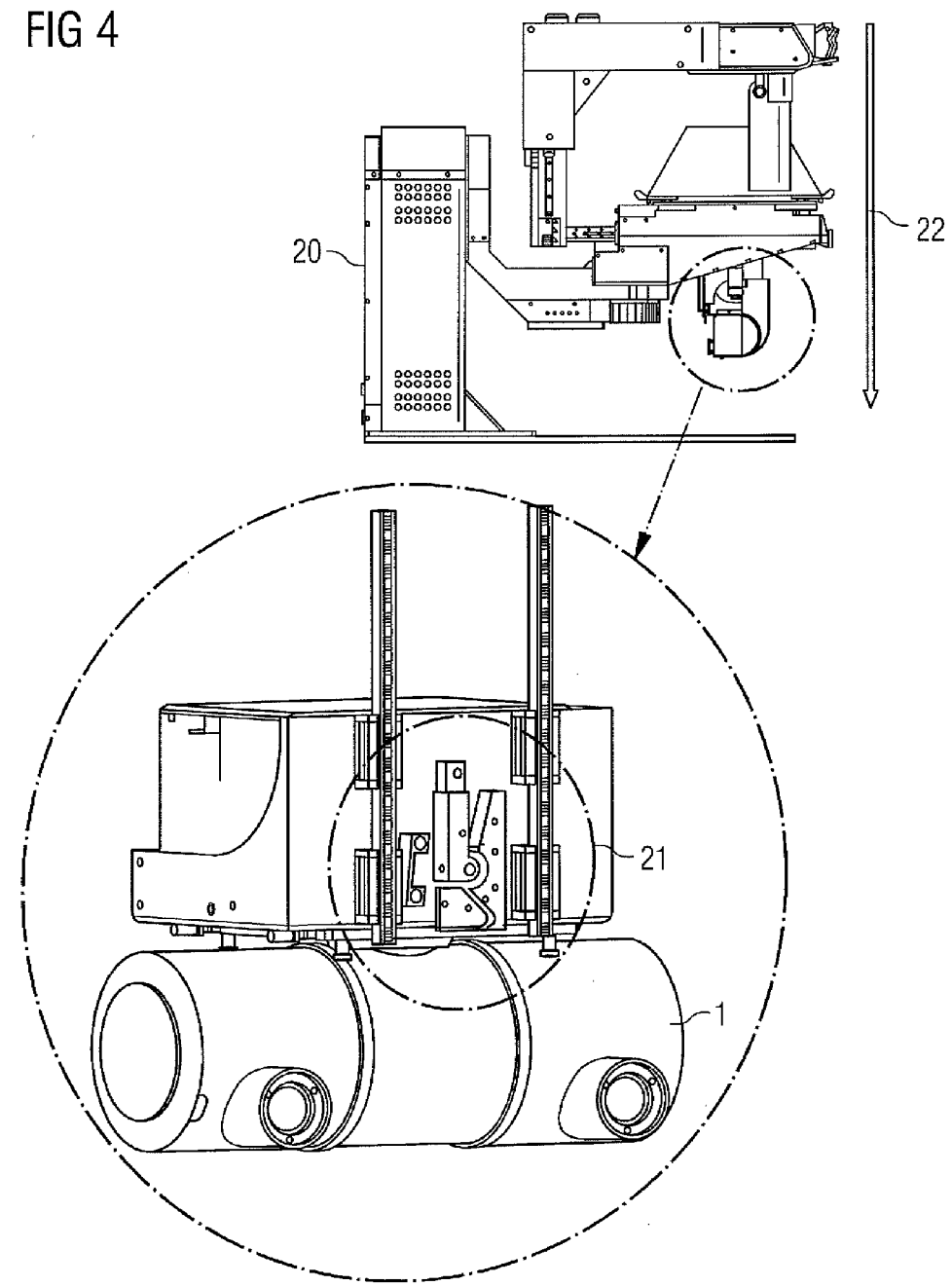
FIG. 4 illustrates the functionality of one embodiment of the x-ray apparatus with an engaging mechanism.

FIG. 3 shows a mechanism used for the partial lowering of the x-ray apparatus. The x-ray tube 1 and the aperture housing 2 form an x-ray apparatus that may be lowered for the patient to climb on. An engaging lever 13, a detent 12 (e.g., with an opening of approximately 30 mm) and a linear guide 14 are shown in FIG. 3. The engaging lever 13, the detent 12, and the linear guide 14 are moved together with the x-ray apparatus 3. The engaging lever 13 includes a ball bearing attached below. The engaging lever 13 has a diameter of 30 mm, for example. The latching lever 13 is also provided with a spring support 23 and is moveably mounted (e.g., pivotable about axis 24) so that the spring support 23 presses the lever 13 into the detent 12 in an engaged position. The detent 12 is a stationary component with respect to the patient support 11. The mechanism is described with the aid of FIG. 4. The x-ray apparatus with the engaging mechanism 21 is visible in the center of FIG. 4. If the emitter is in the engaged position, the x-ray apparatus is in a normal working position. As indicated above right with respect to the entire system 20, the patient support is moved downwards for patient access (e.g., arrow 22). The emitter 1 rests on the floor when the couch moves downwards. Continuing the downward movement provides that the force of the spring on the detent lever 13 is no longer adequate, and the lever is pressed out of the detent 12. At a lower end of the lever is a ball bearing (not shown) that enables the leverage movement. The unit including emitter 1, engaging lever 12, linear guide 14 and spring support may therefore be moved upwards guided by the linear guide 14. If the table is moved upwards again after positioning the patient, the emitter unit reengages on account of the dead weight. No displacement of the emitter outside of a zero degree position arises.

Figure 5:
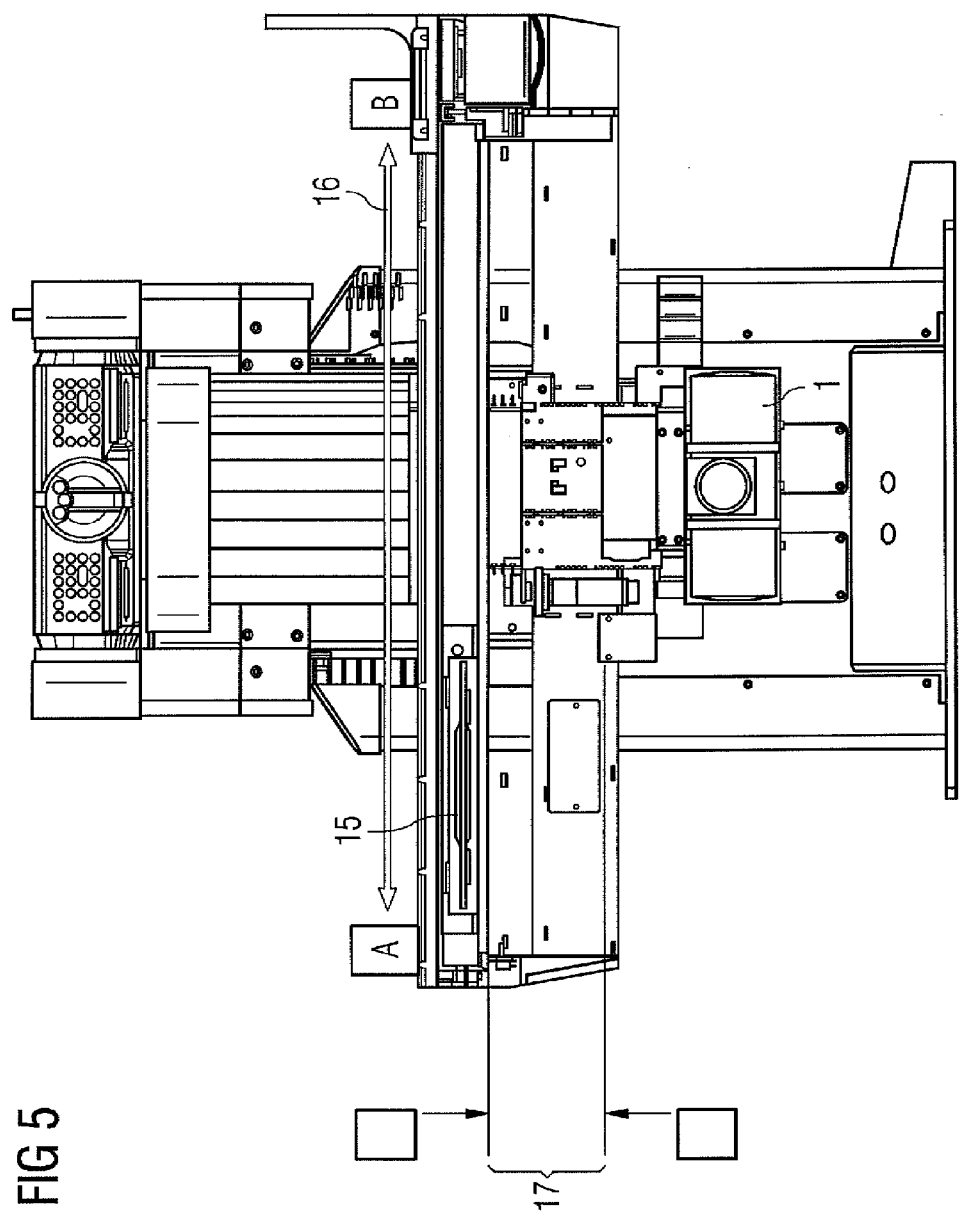
FIG. 5 shows a front view of one embodiment of an under-couch device.

FIG. 5 provides information relating to the space available and/or traveling distance. FIG. 5 shows the emitter 1 in the engaged position (e.g., extended to a maximum). Reference character 17 indicates the maximum upward travelling distance. The maximum upward travelling distance ends just below the detector loader 15, which may traverse the couch from A to B.

Figure 6:
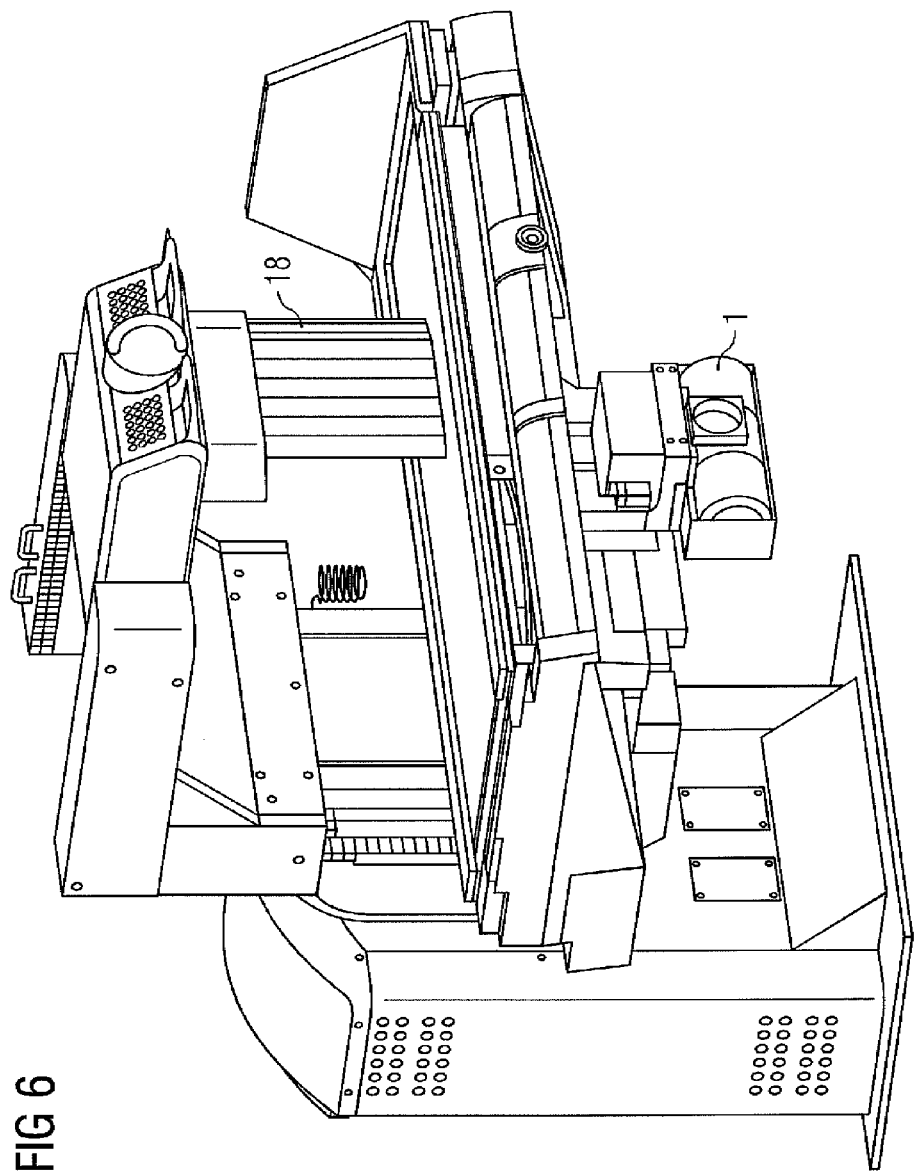
FIG. 6 shows a side view of one embodiment of an under-couch device.

FIG. 6 shows a side view of the overall system, in which protection from x-ray radiation 18 is provided.

Figure 7:
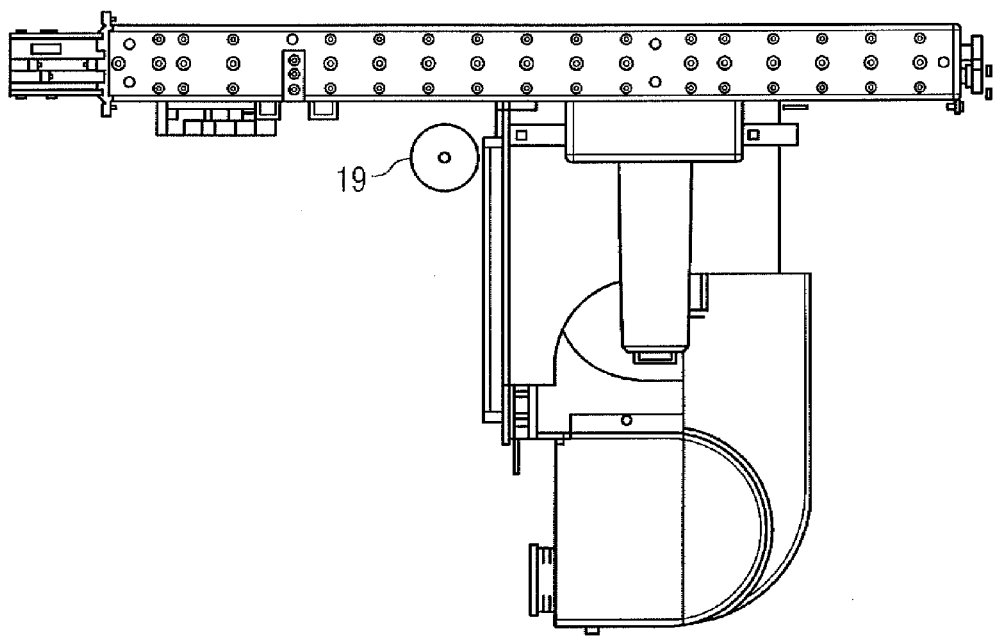
FIG. 7 shows a first example of the positioning of a motor in one embodiment of an apparatus.
Figure 8:
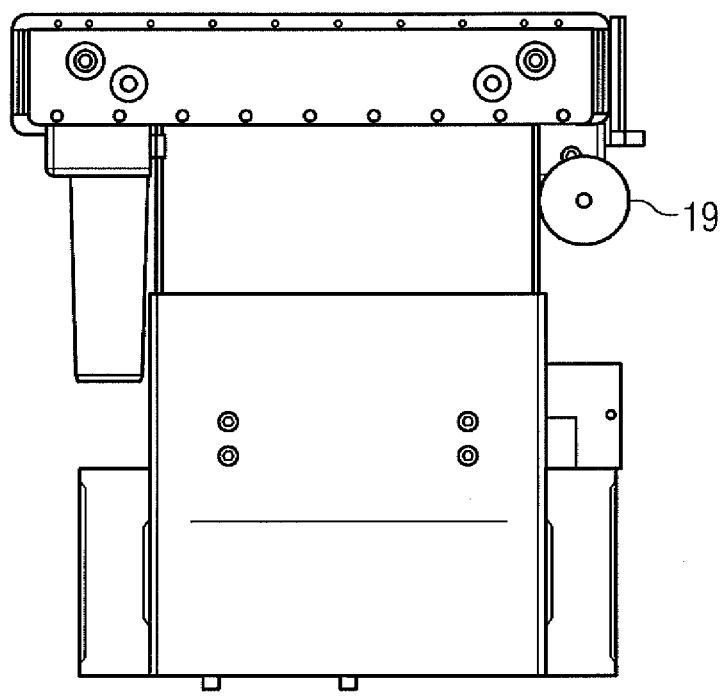
FIG. 8 shows a second example of the positioning of a motor.
Figure 9:
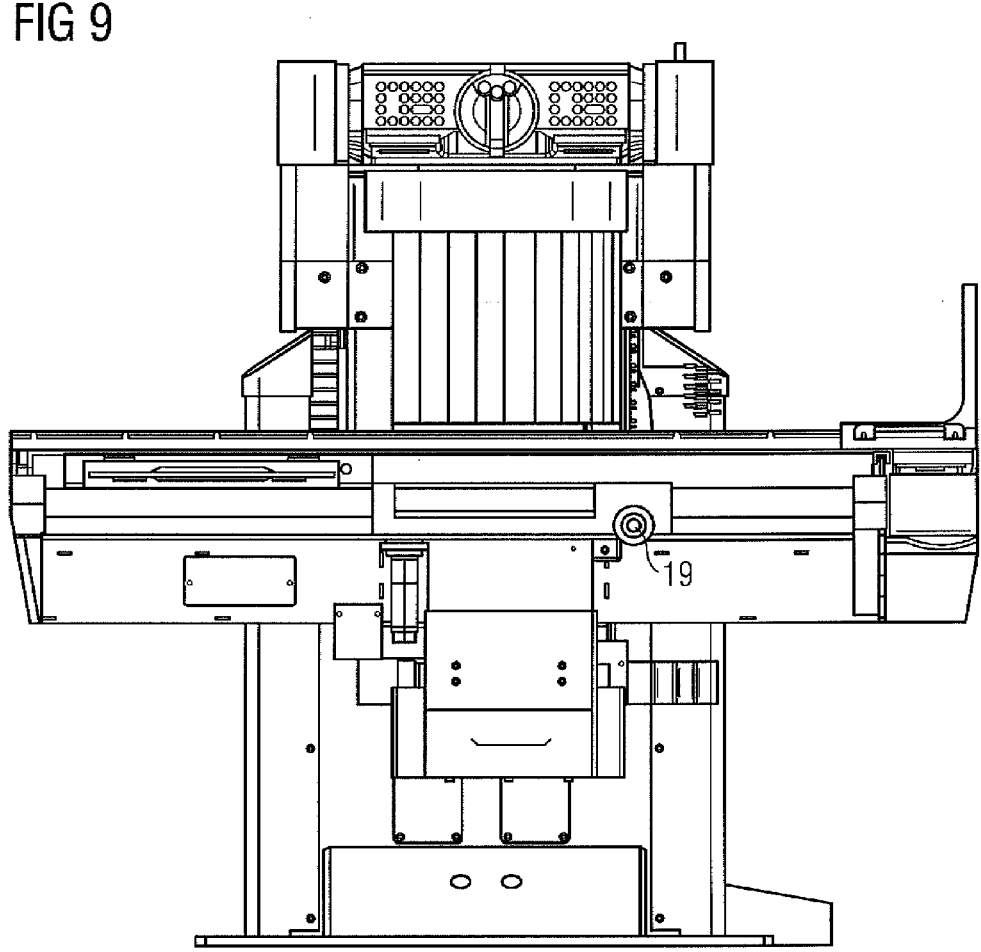
FIG. 9 shows a front view of one embodiment of an under-couch device.
Figure 10:
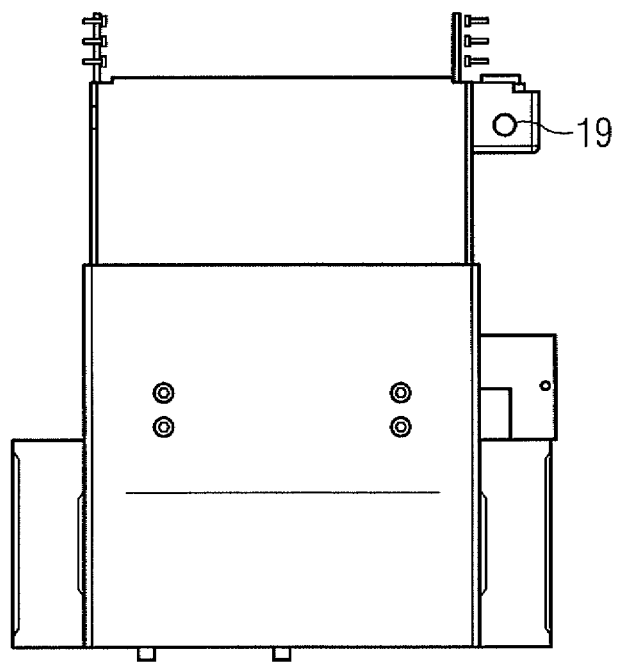
FIG. 10 shows one embodiment of an x-ray apparatus.
Figure 11:
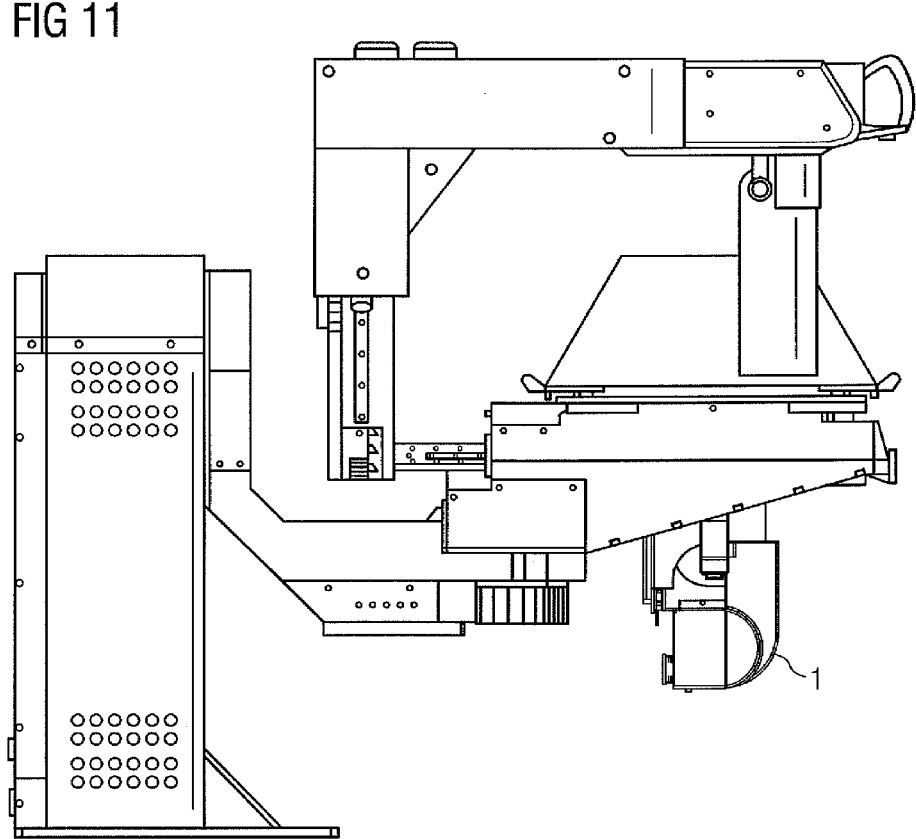
FIG. 11 shows a side view of one embodiment of an under-couch device.

FIG. 7 and FIG. 8 indicate possible positions for the motor-driven drive of the tubes. This drive is designated with reference character 19. Different variants of a motor may be provided (e.g., a space-saving drum motor or a normal electric motor). The type of drive may be a spindle drive or a rack drive. The arrangement of the motor may be lateral to the aperture (e.g., on the rear (FIG. 7) or adjacent to the aperture (FIG. 8) when viewed from the front). FIG. 9 shows the entire system from the front having a possible motor position of the motor 9. FIG. 10 is a front view of the x-ray apparatus, and FIG. 11 is a side view of the entire under-couch system.

The apparatus is not restricted to the embodiments illustrated. For example, other mechanisms than a purely mechanical one may be provided for engagement. Developments may include, for example, a sensor system that detects positions of the couch and triggers an unlocking mechanism using a control signal. The forces developing in the mechanical embodiment illustrated may, for example, be reduced when coming into contact with the floor. In one embodiment, a safety system that prevents the x-ray tube from triggering if no unlocking and/or no engagement and thus no recording position of the x-ray emitter exists, may be applied.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for irradiating patients with x-rays, the apparatus comprising:
    a lowerable patient support;
    an x-ray apparatus that is positionable below the lowerable patient support,
    wherein at least part of the x-ray apparatus moves upwards guided by a guide coupled to the lowerable patient support when the lowerable patient support is lowered.

2. The apparatus as claimed in claim 1, wherein the x-ray apparatus comprises an aperture housing, and
    wherein the lowerable patient support is configured to accommodate at least one part of the aperture housing during lowering of the lowerable patient support.

3. The apparatus as claimed in claim 2, further comprising a mechanism that establishes a releasable contact between the lowerable patient support and the x-ray apparatus such that the x-ray apparatus is subject to a vertical change in position of the lowerable patient support.

4. The apparatus as claimed in claim 2, further comprising a motor for lowering the patient support,
    wherein the x-ray apparatus comprises an aperture housing, and wherein the motor is arranged laterally in the aperture housing.

5. The apparatus as claimed in claim 1, further comprising a mechanism that establishes a releasable contact between the lowerable patient support and the x-ray apparatus such that the x-ray apparatus is subject to a vertical change in position of the lowerable patient support.

6. The apparatus as claimed in claim 5, wherein the releasable contact is configured by effecting a force counteracting a lowering.

7. The apparatus as claimed in claim 6, wherein the mechanism is configured to establish the releasable contact in a defined relative position of the lowerable patient support and the x-ray apparatus.

8. The apparatus as claimed in claim 7, further comprising a safety system,
wherein the safety system is operable to detect whether the releasable contact is established, and
wherein the x-ray apparatus for the x-ray recordings is blocked by the safety system provided the releasable contact is not established.

9. The apparatus as claimed in claim 6, further comprising a safety system,
wherein the safety system is operable to detect whether the releasable contact is established, and
wherein the x-ray apparatus for the x-ray recordings is blocked by the safety system provided the releasable contact is not established.

10. The apparatus as claimed in claim 6, wherein the mechanism comprises a detent and a detent lever.

11. The apparatus as claimed in claim 5, wherein the mechanism is configured for detecting a height and releasing the contact according to a threshold value for the detected height.

12. The apparatus as claimed in claim 11, further comprising a safety system,
wherein the safety system is operable to detect whether the releasable contact is established, and
wherein the x-ray apparatus for the x-ray recordings is blocked by the safety system provided the releasable contact is not established.

13. The apparatus as claimed in claim 11, wherein the mechanism is configured to establish the releasable contact in a defined relative position of the lowerable patient support and the x-ray apparatus.

14. The apparatus as claimed in claim 11, wherein the mechanism comprises a detent and a detent lever.

15. The apparatus as claimed in claim 5, wherein the mechanism comprises a detent and a detent lever.

16. The apparatus as claimed in claim 15, further comprising a safety system,
wherein the safety system is operable to detect whether the releasable contact is established, and
wherein the x-ray apparatus for the x-ray recordings is blocked by the safety system provided the releasable contact is not established.

17. The apparatus as claimed in claim 5, further comprising a safety system,
wherein the safety system is operable to detect whether the releasable contact is established, and
wherein the x-ray apparatus for the x-ray recordings is blocked by the safety system provided the releasable contact is not established.

18. The apparatus as claimed in claim 5, further comprising a motor for lowering the patient support,
wherein the x-ray apparatus comprises an aperture housing, and
wherein the motor is arranged laterally in the aperture housing.

19. The apparatus as claimed in claim 7, wherein the mechanism comprises a detent and a detent lever.

20. The apparatus as claimed in claim 1, further comprising a motor for lowering the patient support,
wherein the x-ray apparatus comprises an aperture housing, and
wherein the motor is arranged laterally in the aperture housing.

* * * * *